United States Patent
Gosheger et al.

(10) Patent No.: US 7,018,411 B2
(45) Date of Patent: Mar. 28, 2006

(54) ENDOPROTHESIS WITH GALVANISED SILVER LAYER

(75) Inventors: Georg Gosheger, Münster (DE); Jens Sass, Buxtehude (DE)

(73) Assignee: Implantcast GmbH, (DE)

( * ) Notice: Subject to any disclaimer, the term of this patent is extended or adjusted under 35 U.S.C. 154(b) by 26 days.

(21) Appl. No.: 10/468,430

(22) PCT Filed: Feb. 18, 2002

(86) PCT No.: PCT/EP02/01705

§ 371 (c)(1),
(2), (4) Date: Feb. 3, 2004

(87) PCT Pub. No.: WO02/065953

PCT Pub. Date: Aug. 29, 2002

(65) Prior Publication Data

US 2004/0134790 A1     Jul. 15, 2004

(30) Foreign Application Priority Data

Feb. 19, 2001   (DE) ................................ 101 07 675

(51) Int. Cl.
*A61F 2/02*       (2006.01)
*A61F 13/00*      (2006.01)
*B32B 15/00*      (2006.01)

(52) U.S. Cl. ................. 623/16.11; 623/23.53; 623/23.57; 623/23.6; 424/422; 424/423; 428/668

(58) Field of Classification Search ...... 623/1.42–1.46, 623/23.53, 23.6, 16.11; 424/422, 423; 428/668

See application file for complete search history.

(56) References Cited

U.S. PATENT DOCUMENTS

| | | |
|---|---|---|
| 3,420,755 A | 1/1969 | Paret |
| 4,274,926 A | 6/1981 | Simon et al. |
| 4,813,965 A | 3/1989 | Roberts |
| 5,492,763 A | 2/1996 | Barry et al. |
| 6,013,106 A * | 1/2000 | Tweden et al. ........... 623/11.11 |
| 6,096,070 A * | 8/2000 | Ragheb et al. ............. 623/1.39 |
| 6,110,204 A * | 8/2000 | Lazarov et al. .......... 623/11.11 |
| 6,534,197 B1 * | 3/2003 | Noda et al. .................. 428/689 |
| 6,582,715 B1 * | 6/2003 | Barry et al. ................. 424/422 |

FOREIGN PATENT DOCUMENTS

EP        0416342        8/1990

* cited by examiner

*Primary Examiner*—David J. Isabella
(74) *Attorney, Agent, or Firm*—Hovey Williams LLP

(57) ABSTRACT

A bone replacement endoprosthesis has a metallic support structure, at least part of the surface of which is galvanically silvered. Beneath the silver layer a bond layer is provided which can comprise gold.

2 Claims, No Drawings

ENDOPROTHESIS WITH GALVANISED SILVER LAYER

BACKGROUND OF INVENTION

1. Field of Invention

The invention relates to an endoprosthesis having a metallic support structure and to a process for producing an endoprosthesis of this type.

2. Discussion of Prior Art

Endoprostheses having a support structure which consists partly or completely of metal are used in a wide range of medical applications, in particular (though not exclusively) in the field of bone replacement. Examples are joint prostheses which are to replace a joint which is no longer functioning and modular systems which can be used to assemble endoprostheses for bone replacement as required and which are used above all in tumor surgery.

When using endoprostheses of this type, it is not possible to rule out the risk of infection. Although it is in principle possible to treat endoprostheses, for example with antibiotics, poor adhesion to the surface, in particular over prolonged periods, and undesirable side effects cause problems.

It is known from U.S. Pat. No. 5,492,763 to use an ion implantation process to introduce metal atoms, such as silver, gold, copper, platinum, iridium, magnesium and palladium, into the surface of an implant structure which consists, for example, of a polymer material. The intention of this process is to achieve a bacteriostatic or bactericidal action. However, ion implantation processes are complex and therefore expensive.

SUMMARY OF THE INVENTION

It is an object of the invention to provide an inexpensive and medically harmless way of reducing the risk of infection in endoprosthesis with a metallic support structure.

This object is achieved by a bone replacement endoprosthesis having the features of claim 1. Advantageous configurations of the invention will emerge from the subclaims.

DETAILED DESCRIPTION OF THE PREFERRED EMBODIMENT

The endoprosthesis according to the invention has a metallic support structure, at least part of the surface of which is electroplated with silver. The endoprosthesis is particularly suitable for bone replacement.

It has been found that the risk of post-implantation infection is minimized by electroplating with silver.

This does not cause any serious side effects. A layer of silver applied by electroplating bonds well to the support structure, so that the infection-inhibiting action of the endoprosthesis is maintained for a long time. Applying a layer of silver by electroplating is relatively inexpensive.

Beneath the layer of silver there is a bonding layer which may, for example, include gold.

A wide range of cast or wrought alloys are suitable as metals for the support structure. Examples include:

cast CoCrMo alloys in accordance with ASTM F 75 or ISO 5832-4,
wrought CoCrMo alloys in accordance with ISO 5832-12,
wrought CoNiCrMo alloys in accordance with ASTM F 562 or ISO 5832-6,
wrought titanium alloys in accordance with ISO 5832-2,
wrought TiAlNb alloys in accordance with ASTM F 1295-92 or ISO 5832-11,
wrought TiAlV alloys in accordance with ASTM F 136 or ISO 5832-3, and
wrought FeCrNiMnMoNbN alloys in accordance with ISO 5832-9.

The choice of a suitable material for the support structure is dependent on the area of use of the endoprosthesis. In accordance with the invention, it is even possible for endoprostheses comprising metals which are not mentioned in the above list to be provided with a surface which has been electroplated with silver.

In the process according to the invention for producing a bone replacement endoprosthesis, a metallic support structure is provided, and at least part of the surface of the support structure is electroplated with silver. Prior to the electroplating with silver, a bonding layer, which may include gold, is applied to the surface which is to be electroplated with silver. It is advantageous for the support structure to be deoxidized in the region of the surface which is to be plated with silver prior to the coating operation.

In an advantageous configuration of the process, a support structure made from a wrought TiAlV alloy is provided. The surface of this support structure which is to be plated with silver is ionically deoxidized in a vacuum chamber, and the deoxidized surface of the support structure is ionically coated with gold in a vacuum chamber. The gold-coated surface of the support structure is then electroplated with silver in an electroplating bath.

In another preferred embodiment of the process according to the invention, a support structure comprising a cast CoCrMo alloy is provided, with the surface of the support structure which is to be plated with silver being deoxidized in an electroplating bath. The deoxidized surface of the support structure is plated with gold in an electroplating bath, and the gold-coated surface of the support structure is plated with silver in an electroplating bath.

The invention is explained in more detail below on the basis of exemplary embodiments.

EXAMPLE 1

In the case of a support structure made from TiAl6V4 in accordance with ISO 5832-3, the oxide layer which is always formed under atmospheric conditions is removed by ion sputtering in a first vacuum chamber (ionic deoxidation). Then, the deoxidized surface of the support structure is ionically coated with gold (gold bombardment) in a second vacuum chamber in a plasma coating process (PVD, physical vapor deposition). The layer of gold protects the surface from being reoxidized, so that the treated support structure can be transported without problems. Finally, a layer of silver is applied to the gold-plated surface in an electroplating bath.

EXAMPLE 2

In the case of a support structure made from special steel or a cast CoCrMo alloy in accordance with ISO 5832-4, the superficial oxide layer is removed by electroplating baths. Then, a gold layer can be applied in the same electroplating bath. The gold-plated surface is then electroplated with silver in a different tank.

What is claimed is:

1. A bone replacement endoprosthesis, comprising:
a metallic support structure made from a cast or wrought alloy,
said support structure presenting a surface, in which at least part of the surface is electroplated with silver and a bonding layer is provided beneath the layer of silver,
said bonding layer comprising gold, without any gold being exposed at the surface.

2. The bone replacement endoprosthesis as claimed in claim 1, wherein the support structure includes at least one material selected from the group consisting of: cast CoCrMo alloys, wrought CoCrMo alloys, wrought CoNiCrMo alloys, wrought titanium alloys, wrought TiAlNb alloys, wrought TiAlV alloys, and wrought FeCrNiMnMoNbN alloys.

* * * * *